US006960695B2

(12) United States Patent
Ellison et al.

(10) Patent No.: US 6,960,695 B2
(45) Date of Patent: Nov. 1, 2005

(54) HYDROFORMYLATION PROCESS

(75) Inventors: Robert Hardy Ellison, Chester (GB); Eric Kragtwijk, Amsterdam (NL); Frederik Hendrik Van Der Steen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 102 days.

(21) Appl. No.: 10/699,075

(22) Filed: Oct. 31, 2003

(65) Prior Publication Data

US 2004/0122262 A1 Jun. 24, 2004

Related U.S. Application Data

(60) Provisional application No. 60/434,921, filed on Dec. 19, 2002.

(51) Int. Cl.[7] .............................................. C07C 45/50
(52) U.S. Cl. ...................... 568/429; 568/444; 568/454
(58) Field of Search ................................ 568/429, 444, 568/454

(56) References Cited

U.S. PATENT DOCUMENTS 3,369,050 A    2/1968  Greene ...................... 260/632
3,420,898 A    1/1969  Van Winkle et al. ....... 260/632
3,440,291 A    4/1969  Van Winkle et al. ....... 260/632
3,448,157 A    6/1969  Slaugh et al. ............... 260/604
3,448,158 A    6/1969  Slaugh et al. ............... 260/604
3,501,515 A    3/1970  Van Winkle et al. ....... 260/439
4,593,141 A *  6/1986  Oswald et al. .............. 568/454

FOREIGN PATENT DOCUMENTS

WO    03/080550 A1   10/2003   ........... C07C/29/16

* cited by examiner

*Primary Examiner*—Samuel Barts
*Assistant Examiner*—Sikarl A. Witherspoon

(57) ABSTRACT

A hydroformylation process comprising reacting a compound having at least one olefinic carbon-to-carbon bond with hydrogen and carbon monoxide in the presence of a cobalt catalyst, the hydroformylation process being carried out in one or more reactors, at least one of which comprises a gas cap region and a liquid-containing region while in use, characterized in that a sulphur-containing additive is present on the inside walls of the gas cap region of the at least one-reactor which comprises a gas cap region and a liquid-containing region. The sulphur-containing additive suppresses the formation of methane during the hydroformylation process.

19 Claims, No Drawings

HYDROFORMYLATION PROCESS

This application claims the benefit of U.S. Provisional Application No. 60/434,921 filed Dec. 19, 2002, the entire disclosure of which is hereby incorporated by reference.

FIELD OF THE INVENTION

The present invention relates to a process for hydroformylating a compound having at least one olefinic carbon-to-carbon bond (also called an olefinic compound herein). In particular, the present invention relates to the production of aldehydes and/or alcohols by the addition of carbon monoxide and hydrogen to an olefinic compound in the presence of a cobalt catalyst.

BACKGROUND OF THE INVENTION

Various processes for producing aldehyde and/or alcohol compounds by the reaction of a compound having at least one olefinic carbon-to-carbon bond with carbon monoxide and hydrogen in the presence of a catalyst are known. Typically, these reactions are performed at elevated temperatures and pressures. The aldehyde and alcohol compounds that are produced generally correspond to compounds obtained by the addition of a carbonyl or carbinol group, respectively, to an olefinically unsaturated carbon atom in the starting material with simultaneous saturation of the olefin bond. Isomerization of the olefin bond may take place to varying degrees under certain conditions with the consequent variation of the products obtained. These processes are typically known as hydroformylation reactions and involve reactions which may be shown in the general case by the following equation:

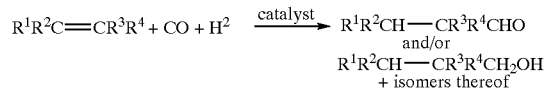

In the above equation, each group $R^1$ to $R^4$ may independently represent an organic radical, for example a hydrocarbyl group, or a suitable atom such as a hydrogen or halogen atom, or a hydroxyl group. The above reaction may also be applied to a cycloaliphatic ring having an olefinic linkage, for example cyclohexene.

The catalyst employed in a hydroformylation reaction typically comprises a transition metal, such as cobalt, rhodium or ruthenium, in complex combination with carbon monoxide and ligand(s) such as an organophosphine.

Representative of the earlier hydroformylation methods which use transition metal catalysts having organophosphine ligands are U.S. Pat. No. 3,420,898, U.S. Pat. No. 3,501,515, U.S. Pat. No. 3,448,157, U.S. Pat. No. 3,440,291, U.S. Pat. No. 3,369,050 and U.S. Pat. No. 3,448,158.

In attempts to improve the efficiency of a hydroformylation process, attention has typically focussed on developing novel catalysts and novel processes for recovering and re-using the catalyst. In particular, novel catalysts have been developed which may exhibit improved stability at the required high reaction temperatures. Catalysts have also been developed which may permit the single-stage production of alcohols rather than a two-step procedure involving separate hydrogenation of the intermediate aldehyde. Moreover, homogeneous catalysts have been developed which may permit improved reaction rates whilst providing acceptable yields of the desired products.

Although steps have been taken to develop improved catalysts, we have detected that some of these catalysts suffer from problems. In particular we have detected that cobalt catalysts comprising cobalt in complex combination with carbon monoxide and a ligand may decompose during the reaction to produce cobalt and/or cobalt carbide (a compound of cobalt and carbon, empirical formula $Co_xC$, where x is 2 or 3). Cobalt carbide is catalytically inactive in hydroformylation reactions, thereby resulting in an increased rate of catalyst usage. The cobalt carbide is not only catalytically inactive in hydroformylation reactions but also has a relatively bulky, porous structure and is insoluble in the reaction medium. This represents a significant disadvantage, particularly for homogeneous cobalt catalysts, because the cobalt carbide typically tends to agglomerate and form detrimental deposits on the internal surfaces of the production facility. The deposition of cobalt carbide and cobalt solids impedes the running of a hydroformylation production facility with optimal efficiency. The presence of these cobalt or cobalt carbide solids also increases the rate of catalyst degradation.

Furthermore, cobalt and cobalt carbide solids present in "dry" spots of the reactor section including the pipework, as is the case in reactors which have a "gas cap" (also known as reactors which are not "liquid-full") may catalyze the following methanation reaction:

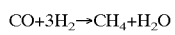

Due to the highly exothermic nature of this reaction, this can lead to an undesirable increase in temperature, which, if left unchecked, can result in a potential safety hazard.

Co-pending U.S. application Ser. No. 10/294,320, filed Nov. 14, 2002, discloses a hydroformylation process comprising reacting a compound having at least one olefinic carbon-to-carbon bond with hydrogen and carbon monoxide in the presence of a cobalt catalyst and a sulfur-containing additive, wherein the additive suppresses the formation of cobalt carbide in the reaction mixture. However there is no disclosure in this application of the problem of cobalt-catalyzed methanation or of any technical solutions to solve the problem of methanation.

SUMMARY OF THE INVENTION

It has now been surprisingly found that we can successfully suppress this undesirable methanation reaction by introducing a sulfur-containing additive onto the inside walls of those reactors which contain "dry spots". The introduction of the sulfur-containing additive is preferably carried out while those reactors are not in use or are "off-line".

According to a first aspect, the present invention provides a hydroformylation process comprising reacting a compound having at least one olefinic carbon-to-carbon bond with hydrogen and carbon monoxide in the presence of a cobalt catalyst, the hydroformylation process being carried out in one or more reactors, at least one of which comprises a gas cap region and a liquid-containing region while in use, characterized in that a sulfur-containing additive is present on the inside walls of the gas cap region of the at least one reactor which comprises a gas cap region and a liquid-containing region.

The process according to the present invention addresses the technical problem of methanation that we have recognised, associated with hydroformylating a compound having an olefinic carbon-to-carbon bond in the presence of a cobalt catalyst. Suitably, the inclusion of the additive on the inside walls of the gas cap region in one or more of the reactors which are not "liquid-full", or which contain a gas cap region and a liquid-containing region, suppresses the formation of methane compared with performing the corresponding hydroformylation reaction in the presence of the cobalt catalyst but without the sulphur-containing additive. Suitably, the additive serves to poison the cobalt and/or cobalt carbide solids which are responsible for the catalysis of the methanation reaction.

DETAILED DESCRIPTION OF THE INVENTION

As used herein the term "gas cap region" means a region within a reactor which consists essentially of gas, that is, a region which generally comprises 95% or greater, preferably 99% or greater, by volume, of gas. In the case of a hydroformylation process the gas present in a gas cap region comprises mainly hydrogen and/or carbon monoxide which are reactants in the hydroformylation process, with up to about 25% by volume of the gas cap region of other gases such as methane, ethane, carbon dioxide and nitrogen. It is in the gas cap region of a reactor where so-called "dry spots" occur on the-walls of the reactor. "Dry spots" are parts of the inside wall of the reactor which have not come into contact with the liquid present in the liquid-containing region of the reactor. It is at these dry spots where methanation can occur due to the deposit of cobalt and cobalt carbide solids which catalyse the methanation reaction.

As used herein the term "reactor comprising a gas cap region and a liquid-containing region while in use" means a reactor which, during the hydroformylation process, comprises a gas cap region which occupies 5% or greater of the volume of the reactor, preferably 10% or greater of the volume of the reactor, most preferably 20% or greater of the volume of the reactor and especially 30% or greater of the volume of the reactor. The remainder of the volume of the reactor comprises liquid, that is, the "liquid-containing region". The liquid-containing region generally comprises the hydroformylation reaction mixture and hydroformylation products. Typically, it is the last stage reactor in a hydroformylation process which contains such a gas cap region and a liquid-containing region while in use. However, any one of the reactors or more than one reactor in a hydroformylation process could contain a gas cap region and a liquid-containing region, as defined herein.

In order to reduce or prevent methanation from occurring, a sulphur-containing additive is present on the inside walls of the gas cap region of the at least one reactor which comprises a gas cap region and a liquid-containing region (referred to hereinafter as the "relevant reactor"). The additive is preferably introduced into the relevant reactor while the latter is off-line or is not in use.

The additive is preferably introduced onto the inside walls of the relevant reactor after it has been cleaned of any solid deposits, for example, during a shut-down of the plant. However, the additive may also be introduced onto the inside walls of the relevant reactor on top of any solid deposits, again preferably during a shut-down of the plant.

The additive may be introduced on to the walls of the relevant reactor in the form of a liquid or gas. From the viewpoint of convenience and control of addition, preferably the additive is introduced on to the walls of the relevant reactor in the form of a liquid, for example, in the form of an aqueous and/or organic solution. Suitably the relevant reactor is filled with an aqueous and/or organic solution of the additive while the reactor is off-line. The solution is left in the reactor for a sufficient amount of time to passivate the cobalt and/or cobalt carbide solids on the walls of the reactor to such an extent that methanation is prevented or reduced to an acceptable level during the hydroformylation process.

As used herein the term "passivate" means that the sulfur-containing additive renders the cobalt and/or cobalt carbide solids inactive in methanation such that methanation is prevented or reduced to an acceptable level. As used herein the term "methanation is prevented or reduced to an acceptable level" means that no uncontrolled temperature excursion can occur. After the solution has been left in the reactor for a sufficient amount of time, the solution should be drained out of the reactor and the reactor should be rinsed with water or an organic solvent in order to remove excess additive.

Alternatively the inside walls of the relevant reactor can be sprayed with an aqueous and/or organic solution of the additive in order to passivate the cobalt and/or cobalt carbide solids on the walls of the reactor with additive. Again, it is necessary to passivate the cobalt and/or cobalt carbide solids on walls of the relevant reactor to such an extent that methanation is prevented or reduced to an acceptable level during the hydroformylation process.

Although not preferred herein, the additive can also be introduced into the relevant reactor in the form of a gas. Suitable gases for use herein include, but are not limited to, hydrogen sulphide, methyl sulphide and COS.

When the additive is introduced in the form of an aqueous or organic solution, the additive is preferably present in solution at a level of from 0.01% to about 40%, more preferably from about 0.1% to about 20%, especially from about 0.1% to about 5%, by weight of solution.

When the additive is introduced in the form of a gas it is preferred that diluted gases are used, but the pure gas can also be used. When diluted gases are used it is preferred that the gas contains at least 0.5 ppmw sulphur. An example of a diluted gas is a mixture of hydrogen sulphide and nitrogen which contains 1% or greater by weight of the hydrogen sulphide gas. The gas is introduced into the relevant reactor for a sufficient amount of time to passivate the cobalt and/or cobalt carbide solids on the walls of the reactor to such an extent that methanation is prevented or reduced to an acceptable level during the hydroformylation process.

The additive can be introduced into the relevant reactor at various intervals, preferably in the range of from once per month to once every 5 years, more preferably from once every 6 months to once every 3 years, especially from once a year to once every 2 years.

The conditions of temperature and pressure at which the additive is introduced into the relevant reactor are not critical and the choice of these conditions are within the ambit of those skilled in the art. Conveniently it is preferred that ambient conditions of temperature and pressure are employed during the introduction of the additive.

During the process of introducing the additive to the inside walls of the gas cap region, for example by soaking the relevant reactor in an aqueous solution of the additive while the relevant reactor is off-line, the whole or part of the inside walls of the liquid-containing region may also become passivated with additive. However the key to the present invention is that the additive is present on the inside walls of the gas-cap region of the relevant reactor during hydroformylation.

In order to minimise the formation of methane it is preferred that at least 70%, preferably at least 80%, more preferably at least 90%, and especially at least 99%, of the surface area of the inside walls of the gas cap region be passivated with additive.

The additive may be an inorganic compound which includes a sulfur atom, preferably in an anion.

A preferred inorganic sulfur-containing additive is any sulfur-containing compound that is capable of forming a sulfide anion ($S^{2-}$) in solution.

Such additives may include a sulfide anion ($S^{2-}$) per se, for example an inorganic sulfide such as sodium sulfide. Alternatively, or additionally, such additives include those compounds which do not include a sulfide anion ($S^{2-}$) per se, but are capable of generating a sulfide anion in aqueous solution, for example sodium hydrogen sulfide.

Thus, preferred inorganic sulfur-containing additives include: metal sulfides, preferably of empirical formula $M_xS_y$ where M is a metal cation and either x is 1 or 2 and y is 1, or x is 2 and y is 3; metal hydrogen sulfides, preferably of empirical formula $M(SH)_z$ where M represents a metal cation and z is 1, 2 or 3; and hydrogen sulfide. Preferably x is 1 or 2 and y is 1. Preferably z is 1 or 2. Suitably, the metal cation M is selected from alkali and alkaline earth metals; preferably from sodium, potassium, calcium, magnesium and zinc. Most preferably the metal cation is potassium, or especially, sodium.

Especially preferred inorganic sulfur-containing additives include sodium sulfide ($Na_2S$), hydrogen sulfide and, especially, sodium hydrogen sulfide (NaHS).

The additive may be an organic sulfur-containing compound. Preferred organic sulfur-containing additives include thiols, disulfides, thioethers and thiophenes. A preferred thiol is represented by the general formula $R^5$—SH, where $R^5$ represents lower alkyl or aryl as defined hereinafter. A preferred disulfide is represented by the general formula $R^6$—SS—$R^7$, wherein $R^6$ and $R^7$ each independently represents lower alkyl or aryl. In highly preferred disulfides both $R^6$ and $R^7$ represent lower alkyl. A preferred thioether is represented by the general formula $R^6$—S—$R^7$ wherein $R^6$ and $R^7$ each independently represent lower alkyl or aryl. Highly preferred thioethers include di(lower alkyl) sulfides, especially dimethyl sulfide. A preferred thiophene is thiophene itself.

Highly preferred organic sulfur-containing additives include dimethylsulfide and thiophene.

An especially preferred sulfur-containing additive is sodium hydrogen sulfide which generates a sulfide anion ($S^{2-}$) in aqueous solution.

The term lower alkyl includes linear or branched, cyclic or acyclic, groups of up to 20 carbon atoms, which may be interrupted by oxygen. Preferably no more than five oxygen atoms are present in an alkyl chain. More preferably there are no oxygen atoms present in the alkyl chain, the chain (or backbone) being made up of only carbon atoms. Optional substituents may include, for example, halo, cyano, hydroxyl, $C_1$–$C_4$ alkoxy, $C_1$–$C_4$ haloalkoxy, ($C_1$–$C_4$ alkoxy) carbonyl, amino and mono- or di—$C_1$–$C_4$ alkylamino groups. When an alkyl group is substituted it preferably has 1–3 substituents. Preferably, however, an alkyl group is unsubstituted. Lower alkyl groups may favourably have up to 16 carbon atoms, preferably up to 10, more preferably up to 6, and most preferably up to 4. Acyclic alkyl groups are preferred. Linear groups are preferred. Preferred lower alkyl groups include the propyl and butyl groups, especially n-propyl and n-butyl, and, most preferred, ethyl and, especially methyl.

The term aryl includes six to ten-membered carbocyclic aromatic groups, such as phenyl and naphthyl, which groups are optionally substituted by one or more substituents, for example 1–3 substituents, preferably selected from halo, cyano, nitro, lower alkyl, lower haloalkyl, $OR^8$, $C(O)R^8$, $C(O)OR^8$ where $R^8$ represents a lower alkyl or aryl group. Preferred aryl groups are unsubstituted. Highly preferred aryl groups are phenyl and tolyl.

The term halo includes fluoro, chloro, bromo and iodo.

Preferably the cobalt catalyst comprises cobalt in complex combination with carbon monoxide and/or an organophosphine. A highly preferred catalyst herein comprises cobalt in complex combination with carbon monoxide and an organophosphine. By the term "complex combination" we mean a coordination compound formed by the union of one or more carbon monoxide and organophosphine molecules with one or more cobalt atoms. In its active form the suitable cobalt catalyst contains the cobalt component in a reduced valence state.

Suitable organophosphine ligands include those having a trivalent phosphorus atom having one available or unshared pair of electrons. Any essentially organic derivative of trivalent phosphorus with the foregoing electronic configuration is a suitable ligand for the cobalt catalyst. It thus will operate as a ligand in forming the desired cobalt catalyst.

Organic radicals of any size and composition may be bonded to the phosphorus atom. For example the organophosphine ligand may comprise a trivalent phosphorus having aliphatic and/or cycloaliphatic and/or heterocyclic and/or aromatic radicals-satisfying its three valences. These radicals may contain a functional group such as carbonyl, carboxyl, nitro, amino, hydroxy, saturated or unsaturated carbon-to-carbon linkages, and saturated and unsaturated non-carbon-to-carbon linkages.

It is also suitable for an organic radical to satisfy more than one of the valences of the phosphorus atom, thereby forming a heterocyclic compound with a trivalent phosphorus atom. For example, an alkylene radical may satisfy two phosphorus valences with its two open valences and thereby form a cyclic compound. Another example would be an alkylene dioxy radical that forms a cyclic compound where the two oxygen atoms link an alkylene radical to the phosphorus atom. In these two examples, the third phosphorus valence may be satisfied by any other organic radical.

Another type of structure involving trivalent phosphorus having an available pair of electrons is one containing a plurality of such phosphorus atoms linked by organic radicals. This type of a compound is typically called a bidentate ligand when two such phosphorus atoms are present, a tridentate ligand when three such phosphorus are present, and so forth.

Suitable cobalt catalysts for use in the process of the present invention and their methods of preparation are disclosed in U.S. Pat. Nos. 3,369,050, 3,501,515, 3,448,158, 3,448,157, 3,420,898 and 3,440,291, all of which are incorporated herein by reference. Preferably, the cobalt catalyst is substantially homogeneous with the reaction mixture.

Preferred cobalt catalysts for use in the process of the present invention are those which include an organic tertiary phosphine ligand, especially a bicyclic heterocyclic tertphosphine ligand, preferably as disclosed in U.S. Pat. No. 3,501,515. Representative examples of such ligands include:

9-hydrocarbyl-9-phosphabicyclo[4.2.1]nonane;

9-aryl-9-phosphabicyclo[4.2.1]nonane, such as 9-phenyl-9-phosphabicyclo[4.2.1]nonane;

(di)alkyl-9-aryl-9-phosphabicyclo[4.2.1]nonane, such as 3,7-dimethyl-9-phenyl-9-phosphabicyclo[4.2.1]-nonane and 3,8-dimethyl-9-phenyl-9-phosphabicyclo[4.2.1]nonane;

9-alkyl-9-phosphabicyclo[4.2.1]nonane,
such as 9-octadecyl-9-phosphabicyclo[4.2.1]nonane,
9-hexyl-9-phosphabicyclo[4.2.1]nonane,
9-eicosyl-9-phosphabicyclo[4.2.1]nonane, and
9-triacontyl-9-phosphabicyclo[4.2.1]nonane;
9-cycloalkyl-9-phosphabicyclo[4.2.1]nonane, such as 9-cyclohexyl-9-phosphabicyclo[4.2.1]nonane and
9-(1-octahydropentalyl)-9-phosphabicyclo[4.2.1]nonane;
9-cycloalkenyl-9-phosphabicyclo[4.2.1]nonane,
such as 9-cyclooctenyl-9-phosphabicyclo[4.2.1]nonane;
9-hydrocarbyl-9-phosphabicyclo[3.3.1]nonane; 9-aryl-9-phosphabicyclo[3.3.1]nonane,
such as 9-phenyl-9-phosphabicyclo[3.3.1]nonane;
9-alkyl-9-phosphabicyclo[3.3.1]nonane,
such as 9-hexyl-9-phosphabicyclo[3.3.1]nonane, and
9-eicosyl-9-phosphabicyclo[3.3.1]nonane.

A particularly preferred ligand includes a tricarbonyl-9-eicosyl-9-phosphabicyclo nonane compound.

A particularly preferred catalyst includes a derivative thereof, believed to be a complex, with cobalt.

The cobalt catalysts can be prepared by a diversity of methods well known to those skilled in the art as disclosed in U.S. Pat. Nos. 3,369,500, 3,501,515, 3,448,157, 3,420,898 and 3,440,291, which are herein incorporated by reference. A convenient method is to combine a cobalt salt, organic or inorganic, with the desired phosphine ligand, for example, in liquid phase followed by reduction and carbonylation. Suitable cobalt salts comprise, for example, cobalt carboxylates such as acetates, octanoates, etc. as well as cobalt salts of mineral acids such as chlorides, fluoride, sulfates, sulfonates, etc. as well as mixtures of one or more of these cobalt salts. The valence state of the cobalt may be reduced and the cobalt-containing complex formed by heating the solution in an atmosphere of hydrogen and carbon monoxide. The reduction may be performed prior to the use of the catalysts or it may be accomplished simultaneously with the hydroformylation process in the hydroformylation zone. Alternatively, the catalysts can be prepared from a carbon monoxide complex of cobalt. For example, it is possible to start with dicobalt octacarbonyl and, by mixing this substance with a suitable phosphine ligand, the ligand replaces one or more of the carbon monoxide molecules, producing the desired catalyst.

The ratio of catalyst to the olefinic compound to be hydroformylated is generally not critical and may vary widely. It may be varied to achieve a substantially homogeneous reaction mixture. Solvents are therefore not required. However, the use of solvents which are inert, or which do not interfere to any substantial degree with the desired hydroformylation reaction under the conditions employed, may be used. Saturated liquid hydrocarbons, for example, may be used as solvent in the process, as well as alcohols, ethers, acetonitrile, sulfolane, and the like. Molar ratios of catalyst to the olefinic compound in the reaction zone at any given instant between about 1:1000 and about 10:1 are found to be satisfactory; a higher or lower ratio of catalyst to olefinic compound may, however, be used, but in general it will be less than 1:1.

The ratio of hydrogen to carbon monoxide may vary widely. In general, a mole ratio of at least about 1, hydrogen to carbon monoxide, is employed. Suitably ratios of hydrogen to carbon monoxide comprise those within the range of from about 1 to 10. Higher or lower ratios may, however, be employed. The ratio of hydrogen to carbon monoxide employed will be governed to some extent by the nature of the reaction product desired. If conditions are selected that will result primarily in an aldehyde product, only one mole of hydrogen per mole of carbon monoxide enters into reaction with the olefinic compound. When an alcohol is the preferred product of the process of the present invention, two moles of hydrogen and one mole of carbon monoxide react with each mole of olefinic compound. The use of ratios of hydrogen to carbon monoxide which are somewhat lower than those defined by these values are generally preferred.

The process of the present invention may be carried, out at various pressures. Consequently, hydroformylation: in accordance with the process of the present invention may typically be carried out at pressures below $7 \times 10^6$ Pa, to as low as $1 \times 10^5$ Pa. The process of the present invention is, however, not limited in its applicability to the lower pressures and pressures in the broad-range from $1 \times 10^5$ Pa up to about $14 \times 10^6$ Pa and in some cases up to about $20 \times 10^6$ Pa, or even higher, may be employed. Typically, the specific pressure used will be governed to some extent by the specific charge and catalyst employed. In general, pressures in the range of from about $2 \times 10^6$ Pa to $10 \times 10^6$ Pa and particularly in the range of from about $2.7 \times 10^6$ Pa to about $9 \times 10^6$ Pa are preferred.

Temperatures employed in the process of the invention will generally range from about 100° C. to about 300° C. and preferably about 150° C. to about 210° C., a temperature of about 200° C. being generally satisfactory. Somewhat higher or lower temperatures may, however, be used within the scope of the invention.

It will be appreciated by those skilled in the art that depending upon the specific charge and cobalt catalyst employed, the process of the present invention may effect the direct, single stage hydroformylation of an olefinic compound to yield a reaction product wherein the alcohols predominate over the aldehydes. By selection of reaction conditions, charge and the cobalt catalyst within the above defined ranges it is possible to obtain greater than or equal to 80% of straight chain alcohols, rather than various branched isomers from the hydroformylation of olefinic compounds. Typically, the alcohols are the desired end product. However, by varying the operating conditions as described hereinbefore the ratio of aldehydes to alcohols product may be varied.

The process of the present invention is generally applicable to the hydroformylation of any aliphatic or cycloaliphatic compound having at least one olefinic carbon-to-carbon bond. Thus, it may be applied to the hydroformylation of olefinic compounds comprising olefinically unsaturated compounds having, for example, from 2 to 19 carbons, to produce reaction mixtures predominating in aliphatic aldehydes and alcohols having one more carbon atom than the starting olefinic compound. Mono-olefinic compounds, such as ethylene, propylene, butylenes, amylenes, hexylenes, heptylenes, octylenes, nonylenes, decylenes, undecylenes, dodecylenes, tridecylenes, tetradecylenes, pentadecylenes, hexadecylenes, heptadecylenes, octadecylenes, nonadecylenes, and their homologues, are examples of suitable unsaturated compounds which may be hydroformylated in the process of the present invention. Suitable unsaturated compounds include both branched and straight-chain compounds having one or more olefinic sites. When two or more double bonds are present these may be conjugated, as in 1,2-hexadiene. In the case of polyolefinic compounds, it is possible to hydroformylate only one of the olefinic sites or several or all of these sites. The unsaturated carbon-to-carbon olefinic linkages may be between terminal and their adjacent carbon atoms, as in 1-pentene, or between internal chain carbon atoms, as in 4-octene.

Preferably an olefinic compound used in the process is a mono-olefinic compound.

Preferably an olefinic compound used in the process has an olefinic linkage between a terminal carbon atom and its adjacent carbon atom.

Hydroformylation of macromolecular materials involving acyclic units of the above types, such as polydiolefinic compounds, for example polybutadiene, as well as copolymers of olefinic and diolefinic compounds, for example styrene-butadiene copolymer, may also be accomplished by the process of the present invention.

Cyclic compounds are equally suitable for use in the process of the present invention. Suitable cyclic compounds include unsaturated alicyclic compounds such as the cyclic olefinic compounds containing carbon-to-carbon unsaturation, such as cyclopentene, cyclohexene, and cycloheptene. Also included in this category are the terpenes and fused-ring polycyclic olefinic compounds, such as 2,5-bicyclo(2,2,1)heptadiene, 1,4,4a,5,8,8a-hexahydro-1,4,5,8-dimethanonaphthalene and the like.

The process of this invention is typically used to hydroformylate olefinic carbon-to-carbon linkages of hydrocarbons but may also be used for non-hydrocarbons. Thus, it is possible to hydroformylate olefinically unsaturated alcohols, epoxides, aldehydes, and acids to corresponding alcohols, aldehydes, and acids containing an aldehyde or hydroxy group on one of the carbon atoms previously involved in the olefinic bond of the starting material. The following are a few specific examples of different types of olefinic compounds that may be hydroformylated by the process of the present invention and the products obtained thereby:

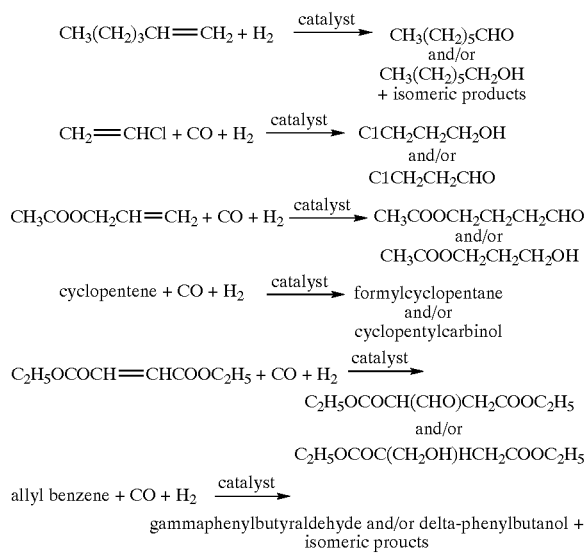

The olefinic charge to the process of the invention may comprise two or more of the above-defined suitable olefinic compounds. Olefinic compounds may be hydroformylated under the conditions defined above to produce mixtures of aldehydes and alcohols in which the alcohols predominate.

The process of the present invention may thus be employed to effect the direct, single stage hydroformylation of olefinic compounds, preferably mono-olefinic compounds, and especially mono-olefins, having, for example, from 2 to 19 carbon atoms per molecule, preferably to produce predominantly terminal alcohols having 5 to 20 carbon atoms per molecule, respectively. Olefinic fractions, such as, for example, polymeric olefinic fractions, cracked wax fractions, and the like, containing substantial proportions of olefinic compounds, may be readily hydroformylated to fractions of hydroformylated products comprising mixtures of predominantly terminal aldehydes and alcohols having one more carbon than the olefinic compounds in the charge and wherein these alcohols are the predominant reaction product. Such suitable feeds consisting of olefinic fractions include, for example $C_7$, $C_8$, $C_9$, $C_{10}$ and higher olefinic fractions as well as olefinic hydrocarbon fractions of wider boiling ranges such as $C_7$–$C_9$, $C_{10}$–$C_{13}$, $C_{14}$–$C_{17}$ olefinic hydrocarbon fractions and the like. In broad terms $C_8$–$C_{16}$ olefinic compounds, in particular $C_8$–$C_{16}$ olefinic hydrocarbons, are preferred.

It will be appreciated that under the above-defined conditions, the olefinic charge may react with carbon monoxide and hydrogen to form reaction products comprising aldehydes and/or alcohols having one more carbon atom per molecule than the olefin charged.

The proportions in which reactants are fed to the reaction zone may vary over relatively wide limits, for example, from about 1 to about 5 molar amounts of an olefinic compound as described hereinbefore may be reacted with from about 1 to about 12 moles of hydrogen and about 1 to about 7 moles of carbon monoxide. Sufficient amounts of olefinic compound are however included in the feed to the reaction zone.

Admixtures of promoters, stabilizers and the like may also be included in the process of the present invention. Thus, minor amounts of phenolic stabilizers such as hydroquinone, alkaline agents such as hydroxides of alkali metals, for example NaOH and KOH, may be added to the reaction zone.

The reaction mixtures obtained may be subjected to suitable catalyst and product separating means comprising one or more steps, for example, stratification, solvent extraction, distillation, fractionation, adsorption, etc. The specific method of product and catalyst separation preferably employed will be governed to some extent by the specific complex and reactants charged. Catalyst or components thereof, as well as unconverted charge, and solvent, when employed, may be recycled in part or entirety to the reaction zone.

The preformed cobalt catalyst, or separate components of the catalyst capable of producing the complex in situ in the reaction zone, may be added to material separated from the reactor which is being recycled to the reaction zone. A part of an alcoholic reaction product may, if desired, be recycled to the reaction zone to function as solvent and/or diluent and/or suspending medium for the catalyst, the catalyst components, and the like, passing to the reaction zone. A part or all of an aldehyde product may optionally be recycled to the reaction zone or may be subjected to hydroformylation conditions in a second and separate reaction zone in the presence of a cobalt catalyst. The cobalt catalyst used in the second hydroformylation step need not be the same as that used in the first step.

According to a further aspect, the present invention provides the use of an additive as defined hereinbefore for suppressing the formation of methane in a hydroformylation reaction employing a cobalt complex catalyst.

The invention will be further described by way of the following non-limiting examples.

EXAMPLES

Comparative Example 1

Methanation activity of cobalt carbide material from a commercial cobalt hydroformylation plant.

Solids taken from a commercial cobalt hydroformylation plant were washed with excess toluene and subsequently dried at 50° C. in vacuo to remove organic residues from the material. The material, hereinafter "Carbide Sample 1, was characterized by X-ray diffraction to consist of ca. 18% cobalt and 82% cobalt carbide. The specific surface area was determined to be ca. 8 m²/g. The methanation acivity of this material was determined by measuring the heat-flow (Watts/g) in an Differential Scanning Coulometry (DSC) apparatus, applying a pressurized measuring cell at 25 bar syngas ($CO/H_2=2$). The higher the heat-flow (Watts/g) the greater the methanation activity. Evolution of a heat-flow started at ca. 200° C., peaking to 50 Watts/g at 350° C. GC analyses of a sample from the gas-phase of the measuring cell showed the presence of methane, showing that a methanation reaction had occurred.

Example 1
Passivation of cobalt carbide material taken from a commercial cobalt hydroformylation plant by treatment with aqueous sodium hydrogen sulfide.

To 1 g Carbide Sample 1, (the same material as described in Comparative Example 1), was added 100 g of a 1% w solution of sodium hydrogen sulfide, NaSH, in water at room temperature. After standing for 6 hours at room temperature, the liquid was decanted and the remaining solids were subsequently washed two times with 100 g water to remove excess NaSH. Elemental analyses showed that the carbide solids contained 2.8 w % of chemically bonded sulphur. DSC measurements on this material showed the absence of any methanation activity.

Comparative Example 2
Methanation activity of cobalt carbide material in the last stage reactor of a commercial cobalt hydroformylation plant A sample taken from the wall in the gas-phase region of a last stage reactor from a commercial cobalt hydroformylation plant was washed with excess toluene and subsequently dried at 50° C. in vacuo to remove organic residues from the material. The material, hereinafter "Carbide Sample 2", was characterized by X-ray diffraction to consist of mixture of cobalt and cobalt carbide. The specific surface area was determined to be ca. 3 m²/g. The methanation activity of this material was determined by measuring the heat-flow (Watts/g) in a Differential Scanning Coulometry (DSC) apparatus, applying a pressurized measuring cell at 25 bar syngas ($CO/H_2=2$). Evolution of a heat-flow started at ca. 200° C., increasing to 2 Watts/g at 300° C.

Example 2
Passivation of cobalt carbide material taken from the gas-phase region in a commercial cobalt hydroformylation plant by treatment with aqueous sodium hydrogen sulfide.

To 0.5 g Carbide Sample 2, (the same material as described in Comparative Example 2), was added 50 g of a 1% w solution of NaSH in water at room temperature. After standing for 6 hours at room temperature, the liquid was decanted and the remaining solids were subsequently washed two times with 50 g water to remove excess NaSH. DSC measurements on this material showed a strong reduction of the methanation activity (heat-flow of 0.4 Watts/g at 300° C.

Comparative Example 3
Methanation activity of cobalt material taken from the liquid-phase region in a reactor of a commercial cobalt hydroformylation plant.

A sample taken from the liquid-phase region in a reactor of a commercial cobalt hydroformylation plant was washed with excess toluene and subsequently dried at 50° C. in vacuo to remove organic residues from the material. The material, hereinafter "Cobalt Sample 1", was characterized by X-ray diffraction to consist of >95% cobalt with traces of cobalt carbide. The specific surface area was determined to be ca. 15 m²/g. The methanation activity of this material was determined by measuring the heat-flow (Watts/g)in an Differential Scanning Coulometry (DSC) apparatus, applying a pressurized measuring cell at 25 bar syngas ($CO/H_2=2$). Evolution of a heat-flow started at ca. 180° C., increasing to 15 Watts/g at 275° C.

Example 3
Passivation of cobalt material taken from the liquid-phase region in a commercial cobalt hydroformylation plant by treatment with aqueous sodium hydrogen sulfide.

To 0.5 g Cobalt Sample 1, (the same material as described in Comparative Example 3), was added 50 g of a 3.5% w solution of NaSH in water at room temperature. After standing for 6 hours at room temperature, the liquid was decanted and the remaining solids were subsequently washed two times with 50 g water to remove excess NaSH. DSC measurements on this material showed a strong reduction of the methanation activity (heat-flow of 0.8 Watts/g at 300° C.

Examples 4–21
Passivation of cobalt carbide material taken from a commercial cobalt hydroformylation plant by treatment with aqueous sodium hydrogen sulfide.

Following the same procedure as described in Example 1, to 1 g Carbide Sample 1, (the same material as described in Comparative Example 1), was added 100 g of an aqueous solution of sodium hydrogen sulfide at room temperature. The concentration of the NaSH solution and the contact time was varied as indicated in Table 1. After standing for the indicated period at room temperature, the liquid was decanted and the remaining solids were subsequently washed two times with 100 g water to remove excess NaSH. The heat generation, as a measure for methanation activity, was determined by DSC measurements on the material after treatment as shown in Table 1.

TABLE 1

| Example | [NaSH] in water (% w) | treating time (h) | Heat-Flux (Watts/g) |
|---|---|---|---|
| 4 | 7.0 | 6 | 0.1 |
| 5 | 3.5 | 6 | 0.1 |
| 6 | 1.75 | 6 | 0.1 |
| 7 | 0.72 | 6 | 0.8 |
| 8 | 0.35 | 6 | 2.1 |
| 9 | 0.07 | 6 | 23 |
| 10 | 0.63 | 0.5 | 0.2 |
| 11 | 0.63 | 1 | 0.2 |
| 12 | 0.63 | 2 | 0.2 |
| 13 | 0.63 | 3 | 0.2 |
| 14 | 0.63 | 4 | 0.2 |
| 15 | 0.63 | 5 | 0.2 |
| 16 | 0.88 | 0.5 | 0.2 |
| 17 | 0.72 | 0.5 | 0.2 |
| 18 | 0.54 | 0.5 | 0.2 |
| 19 | 0.39 | 0.5 | 0.3 |
| 20 | 0.21 | 0.5 | 0.4 |
| 21 | 0.09 | 0.5 | 2.0 |

The Examples 4–21 as listed in Table 1 demonstrate that, provided that sufficient sulphur is present in solution, neither contact time nor NaSH concentration are critical parameters in reduction of methanation activity of cobalt/cobalt carbide solids.

Comparative Example 22

Methanation activity of samples taken from pilot plant operation.

A sample of the Carbide Sample 1 material, (the same as the material of Comparative Example 1), was put in the gas-phase region of the last stage reactor in a pilot plant operating at hydroformylation conditions (60 bar syngas, 200° C.). After three months of operation the sample was removed and the methanation activity was determined by DCS measurements as described in Comparative Example 1. Evolution of a heat-flow started at ca. 225° C., peaking to 14 Watts/g at 375° C., indicating that the solids are still very active in methanation.

Example 22

Methanation activity of NaSH treated samples taken from pilot plant operation.

A sample of Carbide Sample 1 (same as the material described in Comparative Example 1), treated with NaSH as described in Example 2, was placed in the gas-phase region of the last stage reactor of the pilot plant as decribed in Comparative Example 1. The samples were removed after 60 and 160 days of operation and DSC measurements showed that these samples are still inactive in methanation.

Comparative Example 23

Methanation activity of cobalt carbide material from a commercial cobalt hydroformylation plant.

A 25 g sample of Carbide Sample 1, (same as the material described in Comparative Example 1), was loaded into a flow reactor and heated at 240° C. in a flow of syngas. The product gas contained 2.4% methane as measured by GC analysis, formed by methanation on the solids.

Example 23

Passivation of cobalt carbide material from a commercial cobalt hydroformylation plant by dilute hydrogen sulphide.

The flow reactor, filled with 25 g of Carbide Sample 1 material (the same material as described in Comparative Example 1), was operated at 240° C. in a flow of syngas containing 7 ppmv hydrogen sulphide ($H_2S$). The methane concentration in the product gas, gradually dropped from 2.4% to 0.9% after 24 hours, showing a declined methanation activity. Hydrogen sulphide was not detected in the product gas. Subsequently, the concentration of hydrogen sulphide in the syngas was raised to 70 ppmv. After another 24 hours of operation the amount of methane in the product gas had dropped below 0.1% (as measured by GC analysis), while still no hydrogen sulphide was detected in the product gas. After cooling down the solids were removed from the reactor and elemental analyses showed the solids to contain 2.2% w sulphur. Measurement by DSC showed that no exothermic reaction occurred at 25 bar syngas (heat flow at 300° C. is only 0.4 Watts/g).

We claim:

1. A hydroformylation process comprising reacting a compound having at least one olefinic carbon-to-carbon bond with hydrogen and carbon monoxide in the presence of a cobalt catalyst, the hydroformylation process being carried out in one or more reactors, at least one of which comprises a gas cap region and a liquid-containing region while in use, characterized in that a sulphur-containing additive is present on the inside walls of the gas cap region of the at least one reactor which comprises a gas cap region and a liquid-containing region.

2. The process of claim 1 wherein the sulphur-containing additive is introduced on to the inside walls of the gas cap region of the at least one reactor which comprises a gas cap region and a liquid-containing region while said reactor is not in use.

3. The process of claim 2 wherein the additive is introduced on to the walls of the gas cap region of the at least one reactor which comprises a gas cap region and a liquid-containing region in the form of a liquid or gas.

4. The process of claim 1 wherein the additive is introduced on to the walls of the gas cap region of the at least one reactor which comprises a gas cap region and a liquid-containing region in the form of an aqueous and/or organic solution.

5. The process of claim 4 wherein the additive is introduced on to the walls of the gas cap region of the at least one reactor which comprises a gas cap region and a liquid-containing region by spraying an aqueous and/or organic solution of the additive on to the walls of said reactor.

6. The process of claim 4 wherein the additive is introduced on to the walls of the gas cap region of the at least one reactor which comprises a gas cap region and a liquid-containing region by filling said reactor with an aqueous and/or organic solution of the additive.

7. The process of claim 2 wherein the additive is introduced on to the walls of the gas cap region of the at least one reactor which comprises a gas cap region and a liquid-containing region in the form of an aqueous and/or organic solution.

8. The process of claim 7 wherein the additive is introduced on to the walls of the gas cap region of the at least one reactor which comprises a gas cap region and a liquid-containing region by spraying an aqueous and/or organic solution of the additive on to the walls of said reactor.

9. The process of claim 7 wherein the additive is introduced on to the walls of the gas cap region of the at least one reactor which comprises a gas cap region and a liquid-containing region by filling said reactor with an aqueous and/or organic solution of the additive.

10. The process of claim 3 wherein the additive is introduced on to the walls of the gas cap region of the at least one reactor which comprises a gas cap region and a liquid-containing region in the form of an aqueous and/or organic solution.

11. The process of claim 10 wherein the additive is introduced on to the walls of the gas cap region of the at least one reactor which comprises a gas cap region and a liquid-containing region by spraying an aqueous and/or organic solution of the additive on to the walls of said reactor.

12. The process of claim 10 wherein the additive is introduced on to the walls of the gas cap region of the at least one reactor which comprises a gas cap region and a liquid-containing region by filling said reactor with an aqueous and/or organic solution of the additive.

13. The process of claim 1 wherein the additive is an inorganic sulfur-containing additive.

14. The process of claim 13 wherein the inorganic sulfur-containing additive is selected from the group consisting of a metal sulfide, a metal hydrogen sulfide, and hydrogen sulfide.

15. The process of claim 13 wherein the inorganic sulfur-containing additive is selected from the group consisting of sodium hydrogen sulfide, sodium sulfide, and hydrogen sulfide.

16. The process of claim 1 wherein the additive is an organic sulfur-containing additive.

17. The process of claim 16 wherein the organic sulfur-containing additive is selected from the group consisting of thiols, disulfides, thioethers, and thiophenes.

18. The process of claim 17 wherein the organic sulfur-containing additive is selected from the group consisting of dimethylsulfide and thiophene.

19. A method for suppressing the cobalt-catalyzed formation of methane from hydrogen and carbon monoxide in a hydroformylation process carried out in a hydroformylation reactor which comprises introducing a sulfur-containing additive to the inside walls of the hydroformylation reactor.

* * * * *